United States Patent [19]
Corbier et al.

[11] 3,948,815
[45] Apr. 6, 1976

[54] PERFUME COMPOSITIONS
[76] Inventors: Bernard Pierre Corbier, 19 Avenue Fouques; Paul José Teisseire, 14 Avenue Pierre Semard, both of Grasse, France
[22] Filed: Feb. 3, 1975
[21] Appl. No.: 546,564

Related U.S. Application Data
[60] Division of Ser. No. 110,652, Jan. 28, 1971, Pat. No. 3,875,241, which is a continuation-in-part of Ser. No. 585,269, Oct. 10, 1966, Pat. No. 3,578,715.

[30] Foreign Application Priority Data
Oct. 14, 1965  Switzerland.................... 14216/65

[52] U.S. Cl............................. 252/522; 260/586 R
[51] Int. Cl.²...................... A61K 2/46; C11B 9/00
[58] Field of Search.......... 252/522; 260/586, 675.5

[56] References Cited
FOREIGN PATENTS OR APPLICATIONS
1,141,910   5/1969   United Kingdom............ 260/611 R OTHER PUBLICATIONS
Morita et al., J. Org. Chem., 30 (2) 533–538, (1965).

*Primary Examiner*—Herbert Levine
*Assistant Examiner*—G. E. Schmitkons
*Attorney, Agent, or Firm*—Wallenstein, Spangenberg, Hattis & Strampel

[57] ABSTRACT
Novel diketones, illustrative of which is that having the formula

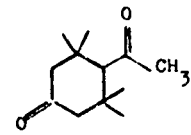

and derivatives thereof, illustrative of which are lower enolethers such as those of the formula

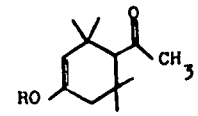

where R represents a lower alkyl group. These compounds possess useful perfume properties.

26 Claims, No Drawings

PERFUME COMPOSITIONS

This is a division of application Ser. No. 110,652, filed Jan. 28, 1971, which matured into U.S. Pat. No. 3,875,241, on Apr. 1, 1975; said application being a continuation-in-part of application Ser. No. 585,269, filed Oct. 10, 1966 which matured into U.S. Pat. No. 3,578,715 on May 11, 1971. The aforesaid patents relate to novel lower enolethers illustrative of which are those of the formula

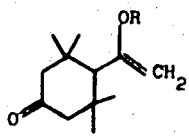

wherein R represents a lower alkyl group. For the sake of clarity, the enolethers of said earlier related application will be clarified as side-chain lower enolethers whereas the enolethers of the present invention will be referred to as ring-substituted lower enolethers.

BRIEF SUMMARY OF THE INVENTION

This invention relates to novel diketones of the general formula

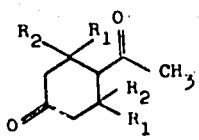   I and also to the corresponding ring-substituted lower enolethers, lower enolesters and ketals of said diketones. In general formula I, $R_1$ and $R_2$ represent lower alkyl or cyclo lower alkyl groups, preferably containing up to 5 carbon atoms, such as methyl, ethyl, propyl, butyl, cyclo propyl or cyclo butyl. The aforementioned ring-substituted lower enolethers, enolesters or ketals of said diketones may, for example contain 1 to 5 carbon atoms in the ether or ester or ketal groups.

The compounds of formula I, their ring-substituted enolethers, enolesters and ketals have interesting and pleasant odors, in particular, they possess woody odors, and accordingly are useful as odorants and can be employed as such in, for example, perfumes, soaps, detergents, cleansing agents and other scented compositions.

DETAILED DESCRIPTION OF THE INVENTION

The invention comprises compounds in accordance with the formula

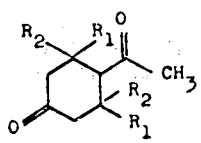   I and also the corresponding ring-substituted lower enolethers lower enolesters and ketals. In these compounds $R_1$ and $R_2$ represent lower alkyl or cyclo lower alkyl groups.

Thus, the invention comprises compounds in accordance with any of the following formulae:

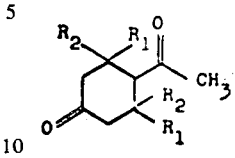   (II)

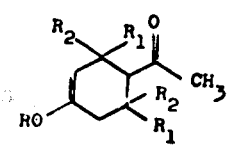   (III)

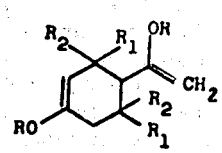   (IV)

or

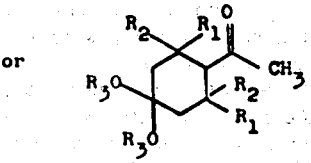   (V)

wherein in each of formulae II to V, R represents a lower alkyl group, $R_1$ and $R_2$, which may be the same or different, represent lower alkyl or cycloloweralkyl groups and the symbols $R_3$ each represent a lower alkyl group or, taken together, a lower alkylene group.

The compounds of the invention of formulae II, III, IV and V possess interesting and useful odoriferous properties. These compounds may accordingly be used alone or, more normally, in admixture with other perfume ingredients and carriers used in perfumes or odorants, in such odoriferous compositions as perfumes, soaps, detergents, cleansing agents and other scented compositions.

The compounds of the invention are of particular interest in that they possess pleasant woody odors.

Special examples of compounds of this invention and their odors are:

The bis-ethylenolether having the formula

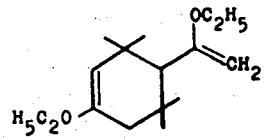   VI i.e. 1-ethoxy-4-(1-ethoxyvinyl)-3,3,5,5-tetramethylcyclo-1-hexene, has a pleasant woody smell.

The monoethylenolether having the formula

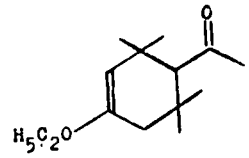   VII i.e. 1-ethoxy-4-acetyl-3,3,5,5-tetramethylcyclo-1-hexene has a highly refined, woody smell, as has the ethylene ketal having the formula

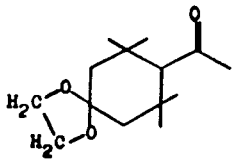 VIII i.e. 4-acetyl-1,1-ethylenedihydroxy-3,3,5,5-tetramethylcyclohexane.

The compounds of this invention may be formulated into perfume compositions in combination with conventional perfume compounding ingredients and, if desired, other perfumes. The amount of a compound of the present invention which may be incorporated into a perfume composition or into a material is not critical. The strength of the odor achieved will depend on the concentration present in the product.

The compounds of the invention may be prepared by reacting a ketone of the general formula

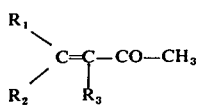 IX in which $R_1$-$R_3$ are as defined above,
with a lower alkyl orthoformate in the presence of an acid catalyst and, if desired, subjecting the reaction product to hydrolysis, ketalization, enol etherification or enol esterification.

The $\alpha,\beta$-unsaturated ketones of formula IX used as starting materials are to a large extent known compounds such as, for example, mesityl oxide, and can be prepared by methods known per se by condensing two ketones which may be the same or different. For example, mesityl oxide can be obtained from acetone by auto-condensation. Other typical starting compounds of formula IX are, for example, those in which $R_1$ and $R_2$ represent ethyl groups whilst $R_3$ represents hydrogen, and those in which $R_1$ is ethyl, $R_2$ methyl, and $R_3$ hydrogen.

The alkyl group of the aforementioned alkyl orthoformate is preferably a lower primary alkyl group with 1 to 5 carbon atoms, such as methyl, ethyl, n-propyl, butyl, iso-butyl, amyl or isoamyl. Suitable acid catalysts are, for example, Lewis acids such as boron trifluoride etherate.

Reaction of the ketone corresponding to formula IX with the alkylorthoformate generally yields a mixture of several enolethers which are distinguished by the different positions of the enolether group. For example, the enolether group can be present in the side chain, as is the case with monoeno lethers having the general formula

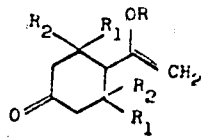 X in which R represents a lower alkyl group, in particular a primary alkyl group with 1 to 5 carbon atoms, and $R_1$ and $R_2$ are lower alkyl groups. The compounds of formula X are claimed in our copending application Ser. No. 565,259 filed Oct. 10, 1966.

On the other hand, the enolether group may be present in the ring, as is the case with monoenolethers having the general formula

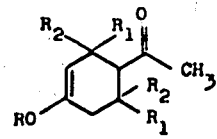 III in which R, $R_1$ and $R_2$ are as defined above.

Finally, enolether groups may be present both in the side chain and in the ring, as is the case with bis-enolethers having the general formula

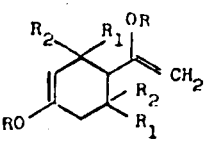 IV in which R, $R_1$ and $R_2$ are as defined above.

The quantitative proportion of these various enolethers is governed both by the reaction conditions and above all by the quantities in which the two starting components are used. In cases where a ketone of formula IX is used in a large excess in relation to the alkylorthoformate, the monoenolethers of formula X will mostly be obtained. If, on the other hand, the two starting components are used in approximately equimolar quantities, the bis-enolethers of formula IX will predominate in the product.

The reaction products can be isolated from the reaction mixture by conventional methods, for example by repeated fractional distillation. Completely pure products can be obtained by methods such as chromatography.

The resulting enolethers of formulae X, III or IV can be converted into the corresponding diketones of formula II by hydrolysis, preferably acid hydrolysis.

If, for example, enolethers corresponding to the formulae

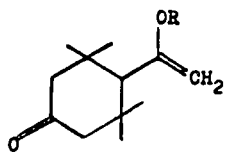 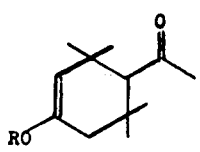 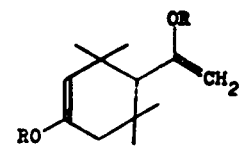

XI XII XIII in which R is as defined above,
are subjected to the action of dilute hydrochloric acid at room temperature, 4-acetyl-3,3,5,5-tetramethylcyclo-hexanone is formed, i.e. the diketone having the formula

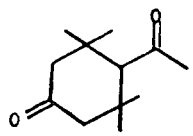

XIV

The diketones thus obtained can be ketalized by methods known per se, for example by reaction with a lower alkylene glycol such as ethylene or propylene glycol, in the presence of an acid agent. There are obtained in this way monoketals corresponding to the general formula

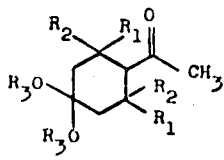

V in which the two symbols $R_3$ each represent a lower alkyl group, preferably containing 1 to 4 carbon atoms, or together represent a lower alkylene group, preferably containing 2 to 4 carbon atoms, whilst the symbols $R_1$ and $R_2$ are as defined above.

For example, one obtains from the diketone of formula XIV ketals of the general formula

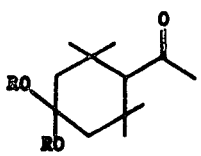

XV in which R is as defined above, for example, 4-acetyl-1,1-dimethoxy-3,3,5,5-tetramethylcyclohexane or 4-acetyl-1,1-ethylenedihydroxy-3,3,5,5-tetramethylcyclohexane.

The diketones of formula II can also be converted by methods known per se into the corresponding enolethers or enolesters. For example, conversion into an enolether can be effected by reaction with a lower alkylorthoformate such as methyl- or ethyl-orthoformate, in the presence of a Lewis acid such as boron trifluoride etherate. For conversion into an enol ester, for example into 1-acetoxy-4-acetyl-3,3,5,5-tetramethylcyclo-1-hexene, the aforementioned diketone can be reacted with a conventional esterifying agent, for instance with a functional derivative of a lower alkane carboxylic acid, illustratively with an anhydride or an ester of such an acid, such as isopropenyl acetate.

In the following Examples, the temperatures are given in degrees Centigrade (°C).

EXAMPLE 1:

1 ml. of boron trifluoride etherate is added to 117.6 g. (1.2 mols) of mesityl oxide. The temperature of the reaction mixture is increased to 50°, 148 g. (1 mol) of ethylorthoformate being added to it over a period of 2 hours. The temperature is kept at 30° for 24 hours, after which 5 g. of powdered sodium carbonate are added and the mixture stirred for 30 minutes. The resulting product is washed once with 100 ml. of a 10% sodium carbonate solution and twice with 100 ml. of a 30% brine solution. A mixture of ethyl alcohol, ethyl formate and excess mesityl oxide is obtained by distillation at normal pressure. The following compounds are obtained as the main products in practically the same quantities:

A. 1-ethoxy-4-(1-ethoxyvinyl)-3,3,5,5-tetramethycyclo-1-hexene; boiling point: 74°–76°/2 mm; $n_D^{15}$: 1.4744; carbonyl index: 220 (theoretical value for one function = 222).

b. 4-(1-ethoxyvinyl)-3,3,5,5-tetramethylcyclohexanone (said (b) compound being described in Example 1 of our aforesaid copending Application and being covered in claims thereof).

EXAMPLE 2

Either of the enolethers obtained in accordance with Example 1 or a mixture thereof is hydrolyzed with 10 times its weight of 0.5% aqueous hydrochloric acid by stirring the mixture for 24 hours at room temperature (approx. 20°–25°). In this way, 75 g. of crude product are obtained from 100 g. of starting product. It is purified by fractional distillation yielding 4-acetyl-3,3,5,5-tetramethylcyclohexanone. Boiling point: 108°/2 mm.; $n_D^{15}$ 1.4786.

EXAMPLE 3

1 mol of 4-acetyl-3,3,5,5-tetramethylcyclohexanone is reacted in benzene solution with 1 mol of ethylene glycol in the presence of p-toluene sulphonic acid. On completion of the reaction, the benzene solution is washed, 4-acetyl-1,1-ethylenedihydroxy-3,3,5,5-tetramethylcyclohexanone being obtained in crystallized form following removal of the benzene. Melting point: 113°–113.5°.

EXAMPLE 4

132.5 g. (1.25 mols) of methylorthoformate are added dropwise at 35 ± 5° over a period of 1 hour to 196 g. (1 mol) of 4-acetyl-3,3,5,5-tetramethylcyclohexanone containing 1 ml. of boron trifluoride etherate. On completion of the addition, the reaction mixture is kept for another 24 hours at the aforementioned temperature. 8 g. of sodium carbonate are then added and the mixture stirred for 15 minutes, after which it is diluted with 1 liter of petroleum ether and washed in the usual way. Following repeated distillations, the following two compounds are obtained in a ratio of 1.4 in a total yield of approximately 80%:

a. 4-acetyl-1-methoxy-3,3,5,5-tetramethylcyclo 1-hexene: Boiling point: 78°–80°/1 mm.; $n_D^{15}$: 1.4780.

b. 4-acetyl-1,1-dimethoxy-3,3,5,5-tetramethylcyclohexane; Boiling point: 90°–93°/1 mm.; Melting point: 59°–60°.

Both these compounds have a pungent cork odor accompanied in the case of (b) by a distinct suggestion of caryophyllenol.

EXAMPLE 5

The following monoenolethers are similarly obtained: 4-acetyl-1-ethoxy-3,3,5,5-tetramethylcyclo-1-hexene; Boiling point: 90°/1 mm.; $n_D^{15}$: 1,4745; this compound smells of cork and carnations, with a trace of geranium. 4-acetyl-1-n-propoxy-3,3,5,5tetramethylcyclo-1hexene; Boiling point: 92°/0.4 mm.; $n_D^{15}$: 1.4749; this compound has a musty odor, reminiscent of patchouli. 4-acetyl-1-n-butoxy-3,3,5,5-tetramethylcyclo-1-hexene; Boiling point 97°–99°/0.44 mm.; $n_D^{15}$: 1.4735; this compound has a pungent, woody odor reminiscent of sandalwood, accompanied by a musty flavor. 4-acetyl-1-isobutoxy-3,3,5,5-tetramethylcyclo-1-hexene; Boiling point 107–109°/0.5 mm.; $n_D^{15}$: 1.4712; this compound has a pungent, musty odor, reminiscent of patchouli. 4-acetyl-1-n-amyloxy-3,3,5,5-tetramethylcyclo-1-hexene; Boiling point 101°–104°/0.3 mm.; $n_D^{15}$: 1,4630; odor weaker than in the preceding examples, but of the same woody, musty flavor. 4-acetyl-1-isoamyloxy-3,3,5,5-tetramethylcyclo-1-hexene; Boiling point 106°–108°/0.2 mm.; $n_D^{15}$: 1.4658; this compound has the same type of odor as the substances described above. 4-acetyl-1-allyloxy-3,3,5,5-tetramethylcyclo-1-hexene; Boiling point 95°–100°/0.5 mm.; $n_D^{15}$: 1.4846; woody smell with a trace of carnations.

In addition, the corresponding ketals can be obtained, such as for example:

4-acetyl-1,1-diethoxy-3,3,5,5-tetramethylcyclohexane; Boiling point 104°/1 mm.; $n_D^{15}$: 1.4676.

4-acetyl-1,1-di-n-propoxy-3,3,5,5-tetramethylcyclohexane; Boiling point 118°/0.4 mm.; $n_D^{15}$: 1.4676.

4-acetyl-1,1-di-n-butoxy-3,3,5,5-tetramethylcyclohexane;
Boiling point 125°–127°/0.4 mm; $n_D^{15}$ 1.4662; weak, woody flavor.

4-acetyl-1,1-di-isobutoxy-3,3,5,5tetramethylcyclohexane; Boiling point 125-128°/0.5 mm.; Melting point 48°.

EXAMPLE 6

1-acetoxy-4-acetyl-3,3,5,5-tetramethylcyclo-1-hexene (b.p. 92°–94°/0.3 mm.; $n_D^{15}$: 1.4785) is obtained by reacting 4-acetyl-3,3,5,5-tetramethylcyclohexanone with isopropenyl acetate. This compound is distinguished by its very refined, but slightly woody and amber-like odor.

EXAMPLE 7

Starting from mesityl oxide and methylorthoformate, the procedure described in Example 1 yields a mixture from which the bis-enolether, 1-methoxy-4-(1-methoxyvinyl)-3,3,5,5-tetramethylcyclo-1-hexene is isolated; boiling point 82°–84°/1 mm., $n_D^{15}$: 1.4872.

EXAMPLE 8

Starting from mesityl oxide and n-propylorthoformate, the procedure described in Example 1 yields a mixture of the corresponding n-propylenolethers boiling at 95°–100°/1 mm., $n_D^{15}$: 1.47954. Its odor is similar to that of the corresponding mixture of Example 1.

EXAMPLE 9

Starting from mesityl oxide and isobutylorthoformate, the procedure described in Example 1 yields a mixture of the corresponding isobutylenolethers boiling at 110°–120°/1 mm.; $n_D^{15}$: 1.4775. Its odor is similar to that of the corresponding mixture of Example 1, although somewhat stronger.

EXAMPLE 10

Starting from mesityl oxide and isoamylorthoformate, the procedure described in Example 1 yields a mixture of the corresponding isoamylenolethers boiling at 110°–120°/1 mm.; $n_D^{15}$: 1.4780. Its odor is similar to that of the corresponding mixture of Example 1, although slightly weaker.

EXAMPLE 11

0.8 ml of etherate of boron trifluoride are added to 496 g (4 moles) of cyclopropyl-4-pentene-3-one-2. The temperature of the mixture is brought up to 50°C and after 4 hours 118.4 g (0.8 mole) of ethyl orthoformiate is added. The temperature is maintained at 50°C for 4 hours. The solvent is then removed in a boiling water bath under reduced pressure (20 mm of Hg). There is obtained 550 g of crude product containing excess cyclopropyl-4-pentene-3-one-2 which is recovered by distillation.

The residue remaining after the distillation (121.5 g) is distilled under a pressure of 0.5 mm of Hg. 100 g of product distills over in the range from 110°–124°C. The product shows $$n_D^{15} = 1,5110.$$

Chromatographic analysis of the vapour phase indicates the presence of 4-acetyl-3,5-dimethyl-3,5-dicyclopropyl-cyclohexanone;

4-(ethoxy-vinyl)-3,5-dimethyl-3,5-dicyclopropylcyclohex-1-ene and 1-ethoxy-4-(1-ethoxy-vinyl)-3,5-dimethyl-3,5-dicyclopropylcyclohex-1-ene.

The infra-red spectrum of the product is as follows: $(CH_2)$ 3000, 3078 and 3110 $cm^{-1}$; $(CH_2)$ 1010 $cm^{-1}$; (CO) 1705 $cm^{-1}$ (strong band): (C=C) 1660 and 1642 $cm^{-1}$ (2 strong bands); (C-O) 1235 and 1295 $cm^{-1}$; (C-H) 3078 $cm^{-1}$; (C=C) 1640 $cm^{-1}$; (-H) 820 $cm^{-1}$ and (CH 795 $cm^{-1}$.

The crude product thus obtained can be used directly in this condition in the preparation of perfume compositions. The crude product had a strong ambergris/timber smell.

EXAMPLE 12

Some odorant compositions containing a mixture of 4-(1-ethoxyvinyl)-3,3,5,5-tetramethylcyclohexanone (substance A) and 1-ethoxy-4-(1-ethoxyvinyl)-3,3,5,5-cyclo-1-hexene (substance B), are described in the following:

|  | PARTS BY WEIGHT |
|---|---|
| a) Mixture of substances A and B | 100 |
| Benzyl salicylate | 200 |
| p-cresylacetate (10%) in diethyl phthalate | 10 |
| $C_{16}$—aldehyde in diethyl phthalate (10%) | 10 |
| Geraniol extra | 40 |
| Benzyl acetate | 50 |
| α-ionone | 100 |
| Diethylacetophenone | 25 |
| Phenyl oxide | 10 |
| Linalyl acetate | 150 |

Continued

| | PARTS BY WEIGHT |
|---|---|
| Cinnamic alcohol | 30 |
| Coumarin | 50 |
| b) Mixtures of substances A and B | 150 |
| Diisobutyl carbinol acetate | 200 |
| Eugenol extra | 50 |
| Methylnonyl acetaldehyde (10%) in Diethyl phthalate | 30 |
| C₁₆—aldehyde (10%) in diethyl phthalate | 10 |
| Phenylethyl acetate | 30 |
| Amyl cinnamic aldehyde | 20 |
| Benzyl acetate | 40 |
| α-ionone | 100 |
| Hydroxycitronellal | 70 |
| Geranium-Bourbon essence | 70 |
| Geraniol extra | 30 |
| Citronellol | 30 |
| Coumarin | 20 |

We claim:

1. A perfume composition containing a compound having the formula

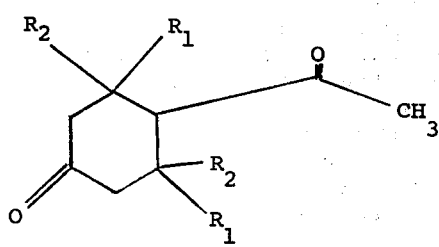

or its corresponding ring substituted lower enolethers, lower enolesters and ketals, $R_1$ and $R_2$ representing lower alkyl or cyclo lower alkyl groups.

2. A perfume composition containing a compound having the formula

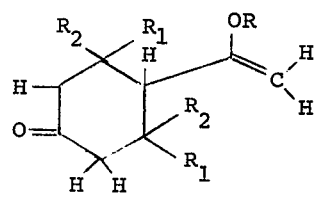

in which R represents a lower alkyl group, $R_1$ and $R_2$ represent lower alkyl.

3. A perfume composition containing a compound having the formula

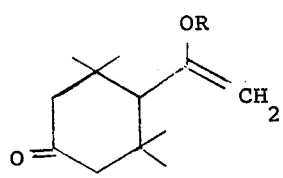

in which R represents a lower alkyl group.

4. A perfume composition containing a compound in accordance with any one of the following formulae:

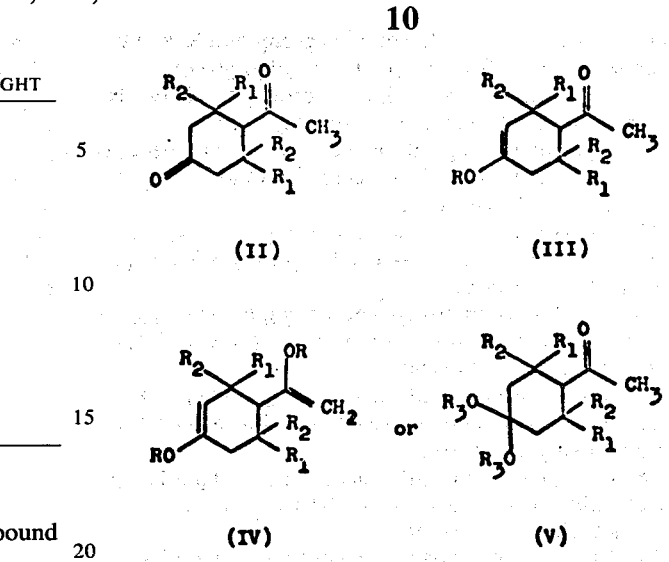

wherein R in each of formulae II to V represents a lower alkyl group, $R_1$ and $R_2$ represent lower alkyl or cyclolower alkyl groups and the symbols $R_3$ each represent a lower alkyl group or, taken together, a lower alkylene group, together with one or more other perfume ingredients and/or carriers and/or diluents commonly used in perfume compositions.

5. A perfume composition according to claim 4, wherein the groups R, $R_1$ and $R_2$ all represent alkyl groups containing from 1 to 5 carbon atoms.

6. A perfume composition according to claim 4, wherein the groups R, $R_1$ and $R_2$ all represent methyl groups.

7. A perfume composition according to claim 4, wherein said compound has the formula

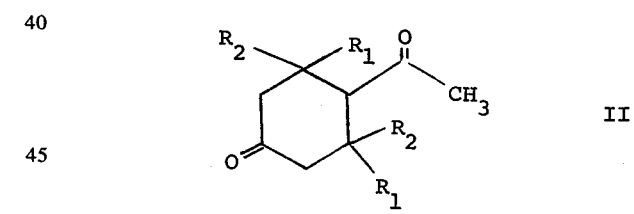

wherein $R_1$ and $R_2$ represent lower alkyl or cyclolower alkyl groups.

8. A perfume composition according to claim 7, in which said compound is 4-acetyl-3,3,5,5-tetramethylcyclohexanone.

9. A perfume composition according to claim 7, in which said compound is 4-acetyl-3,5-dimethyl-3,5-dicyclopropylcyclohexanone.

10. A perfume composition according to claim 4, wherein said compound has the formula

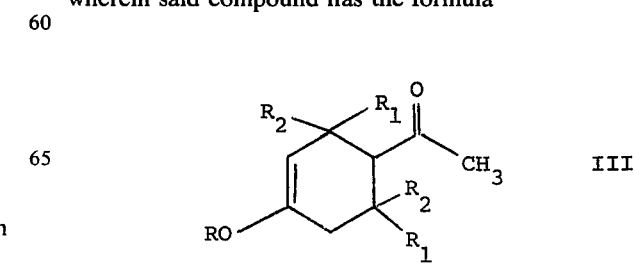

wherein R represents a lower alkyl group and $R_1$ and $R_2$ represent lower alkyl or cyclolower alkyl groups.

11. A perfume composition according to claim 10, wherein $R_1$ and $R_2$ represent methyl groups.

12. A perfume composition according to claim 10, in which said compound is 4-acetyl-1-methoxy-3,3,5,5-tetramethylcyclo-1-hexene.

13. A perfume composition according to claim 10, in which said compound is 4-acetyl-1-ethoxy-3,3,5,5-tetramethylcyclo-1-hexene.

14. A perfume composition according to claim 10, in which said compound is 4-acetyl-1-n-propoxy-3,3,5,5-tetramethylcyclo-1-hexene.

15. A perfume composition according to claim 10, in which said compound is 4-acetyl-1-n-butoxy-3,3,5,5-tetramethylcyclo-1-hexene.

16. A perfume composition according to claim 10, in which said compound is 4-acetyl-1-isobutoxy-3,3,5,5-tetramethylcyclo-1-hexene.

17. A perfume composition according to claim 10, in which said compound is 4-acetyl-1-allyloxy-3,3,5,5-tetramethylcyclo-1-hexene.

18. A perfume composition according to claim 4, wherein said compound has the formula

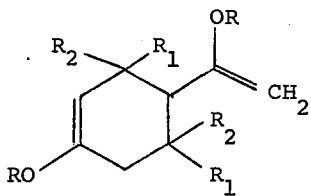

wherein R represents a lower alkyl group and $R_1$ and $R_2$ represent lower alkyl groups or cycloloweralkyl groups.

19. A perfume composition according to claim 18, wherein $R_1$ and $R_2$ represent methyl groups.

20. A perfume composition according to claim 18, in which said compound is 1-ethoxy-4-(1-ethoxyvinyl)-3,3,5,5-tetramethylcyclo-1-hexene.

21. A perfume composition according to claim 18, in which said compound is 1-ethoxy-4-(1-ethoxyvinyl)-3,5-dimethyl-3,5-dicyclopropylcyclo-1-hexene.

22. A perfume composition according to claim 4, wherein said compound has the formula

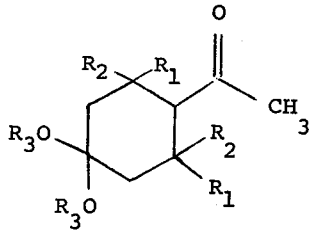

wherein $R_1$ and $R_2$ represent lower alkyl or cyclo lower alkyl groups and the symbols $R_3$ each represent lower alkyl or, taken together, a lower alkylene group.

23. A perfume composition according to claim 22, wherein $R_1$ and $R_2$ represent methyl groups.

24. A perfume composition according to claim 22, in which said compound is 4-acetyl-1,1-dimethoxy-3,3,5,5-tetramethylcyclohexane.

25. A perfume composition according to claim 22, in which said compound is 4-acetyl-1,1-ethylenedioxy-3,3,5,5-tetramethylcyclohexane.

26. A perfume composition containing the compound 4-(1-ethoxyvinyl)-3,3,5,5-tetramethylcyclohexanone.

* * * * *